United States Patent
Hammerschmidt et al.

(10) Patent No.: US 10,215,691 B2
(45) Date of Patent: Feb. 26, 2019

(54) RADAR SPECTROSCOPY BASED GAS SENSOR

(71) Applicant: Infineon Technologies AG, Neubiberg (DE)

(72) Inventors: Dirk Hammerschmidt, Villach (AT); Robert Hermann, Voelkermarkt (AT)

(73) Assignee: Infineon Technologies AG, Neubiberg (DE)

( * ) Notice: Subject to any disclaimer, the term of this patent is extended or adjusted under 35 U.S.C. 154(b) by 113 days.

(21) Appl. No.: 15/352,278

(22) Filed: Nov. 15, 2016

(65) Prior Publication Data

US 2018/0136120 A1 May 17, 2018

(51) Int. Cl.
*G01N 21/3504* (2014.01)
*G01N 22/00* (2006.01)
*G01N 21/17* (2006.01)

(52) U.S. Cl.
CPC ......... *G01N 21/3504* (2013.01); *G01N 22/00* (2013.01); *G01N 2021/1704* (2013.01)

(58) Field of Classification Search
CPC ....... G01N 21/3504; G01N 2001/2279; G01N 2291/0215; G01N 33/0031; G01N 33/004
See application file for complete search history.

(56) References Cited

U.S. PATENT DOCUMENTS

| | | | | |
|---|---|---|---|---|
| 5,015,099 A * | 5/1991 | Nagai | ..................... | G01N 21/39 250/338.5 |
| 5,173,749 A * | 12/1992 | Tell | ..................... | G01N 21/031 250/343 |
| 5,381,010 A * | 1/1995 | Gordon | ..................... | G01J 1/16 250/339.13 |
| 8,004,682 B2 | 8/2011 | Weber et al. | | |
| 9,869,632 B2 * | 1/2018 | Bitter | ..................... | G01N 21/31 |

* cited by examiner

*Primary Examiner* — David P Porta
*Assistant Examiner* — Faye Boosalis
(74) *Attorney, Agent, or Firm* — Harrity & Harrity, LLP (57) ABSTRACT

A gas sensor includes a transmitter that may transmit a first radar signal, associated with a resonance peak corresponding to a first gas, through a space including the first gas and a second gas. The first gas may absorb a portion of the first radar signal to create a second radar signal. The transmitter may transmit a first infrared (IR) signal, associated with a second resonance peak corresponding to the second gas, through the space. The first gas or the second gas may absorb a portion of the first IR signal to create a second IR signal. The gas sensor may include a controller to determine a concentration of the second gas based on the second radar signal and the second IR signal.

20 Claims, 4 Drawing Sheets

RADAR SPECTROSCOPY BASED GAS SENSOR

BACKGROUND

A spectroscopic sensor may be used to measure a concentration of a gas by determining an amount of signal, at a known frequency or wavelength, that is absorbed when the signal is transmitted through a space that includes the gas.

SUMMARY

According to some possible implementations, a gas sensor may include a transmitter to: transmit a first radar signal, associated with a resonance peak corresponding to a first gas, through a space including the first gas and a second gas, where the first gas is to absorb a portion of the first radar signal to create a second radar signal; transmit a first infrared (IR) signal, associated with a second resonance peak corresponding to the second gas, through the space, where the first gas or the second gas to absorb a portion of the first IR signal to create a second IR signal; and a controller to determine a concentration of the second gas based on the second radar signal and the second IR signal.

According to some possible implementations, a gas sensor may include a transmitter to: transmit a first radar signal, associated with a resonance peak corresponding to a gas, through a space including the gas, where the gas is to absorb a portion of the first radar signal to create a second radar signal, where the first radar signal is to be transmitted through an enclosure, during transmission of the first radar signal through the space, that permits the gas to enter a hollow portion of the enclosure; and a controller to determine a concentration of the gas based on the second radar signal.

According to some possible implementations, a radar-based gas sensor may include a transmitter to: transmit a first radar signal, associated with a first resonance peak corresponding to a first gas, through a hollow portion of an enclosure that includes the first gas and a second gas, where the first gas is to absorb a portion of the first radar signal to create a second radar signal; transmit a first infrared (IR) signal, associated with a second resonance peak corresponding to the second gas, through the hollow portion of the enclosure, where the first gas or the second gas is to absorb a portion of the first IR signal to create a second IR signal; and a controller to determine a concentration of the second gas based on the second radar signal and the second IR signal.

DETAILED DESCRIPTION

The following detailed description of example implementations refers to the accompanying drawings. The same reference numbers in different drawings may identify the same or similar elements.

An infrared (IR) based spectroscopic sensor may be used to measure a concentration of a gas. The IR transmitter may transmit an IR signal (i.e., IR light) through a space to an IR receiver. The space may include the gas to be measured. Based on the IR signal received by the IR receiver (i.e., based on the amount of IR signal absorbed by the gas), the concentration of the gas may be determined.

An IR-based spectroscopic gas sensor that is associated with measuring a concentration of a particular gas may exhibit cross-sensitivity to one or more other gases, however. For example, when an IR-based spectroscopic gas sensor is used to measure a concentration of carbon dioxide ($CO_2$) in ambient air, the measured concentration may be sensitive to other gases present in the ambient air (e.g., carbon monoxide (CO), water vapor ($H_2O$), oxygen ($O_2$), ozone ($O_3$), or the like).

The cross-sensitivity may result because the IR signal, transmitted by the IR-based spectroscopic gas sensor, can span a range of frequencies that include resonance peaks for the particular gas to be measured, as well as resonance peaks for one or more of the other gases. A resonance peak is a frequency of signal at which a gas molecule (e.g., $CO_2$, CO, $H_2O$, $O_2$, $O_3$, etc.) is caused to vibrate such that an amount of energy from the signal is absorbed by the gas molecule. An IR signal that spans multiple resonance peaks (e.g., a broadband IR spectrum) corresponding to different gases may cause molecules of multiple gases to absorb the IR signal, thereby reducing an accuracy of a measured concentration for a particular gas. For example, the measured concentration for the particular gas may be an average of all absorptions in the broadband IR spectrum frequency range (weighted by a spectral density of the broadband IR spectrum).

In some cases, including one or more IR filters in the IR-based spectroscopic gas sensor may allow the range of the transmitted IR signal to be narrowed (e.g., such that the transmitted IR signal spans a smaller number of resonance peaks). However, the use of IR filters may lead to increased cost and/or complexity of the IR-based spectroscopic gas sensor because multiple detectors, signal processing components, or the like, are also needed. Moreover, IR transmitters may degrade significantly (e.g., due to aging effects), causing accuracy drift in association with heating-cooling-heating cycles during operation.

Implementations described herein provide a radar-based spectroscopic gas sensor that may be used to determine a concentration of a gas. In some implementations, the radar-based spectroscopic gas sensor (herein referred to as a radar-based gas sensor) may be used to determine a concentration of a particular gas. Additionally, or alternatively, the radar-based gas sensor may be used to correct or supplement a determination of a gas concentration measured by an IR-based spectroscopic gas sensor, as described below. In some implementations, information that identifies concentrations of one or more gases may be used to control a system (e.g., an automotive system).

In some implementations, a radar transmitter, included in the radar-based gas sensor, may be configured to emit a radar signal within a narrow frequency range that covers a resonance peak associated with a particular gas (i.e., the radar transmitter may be configured to emit a selective spectrum), thereby reducing and/or removing cross-sensitivities associated with one or more other gases.

Moreover, the selective spectrum capability may deliver a higher spectral density for a given amount of power (e.g., as compared to the broadband IR spectrum corresponding to the same amount of power), which may result in improved measurement of the gas concentration without increasing power consumption.

Additionally, or alternatively, the radar-based gas sensor may have increased reliability as compared to an IR-based gas sensor and/or another type of gas sensor. For example, a radar antenna of a radar-based gas sensor may not experience significant degradation or aging effects (e.g., as compared to an IR transmitter or an IR receiver).

Figure 1:
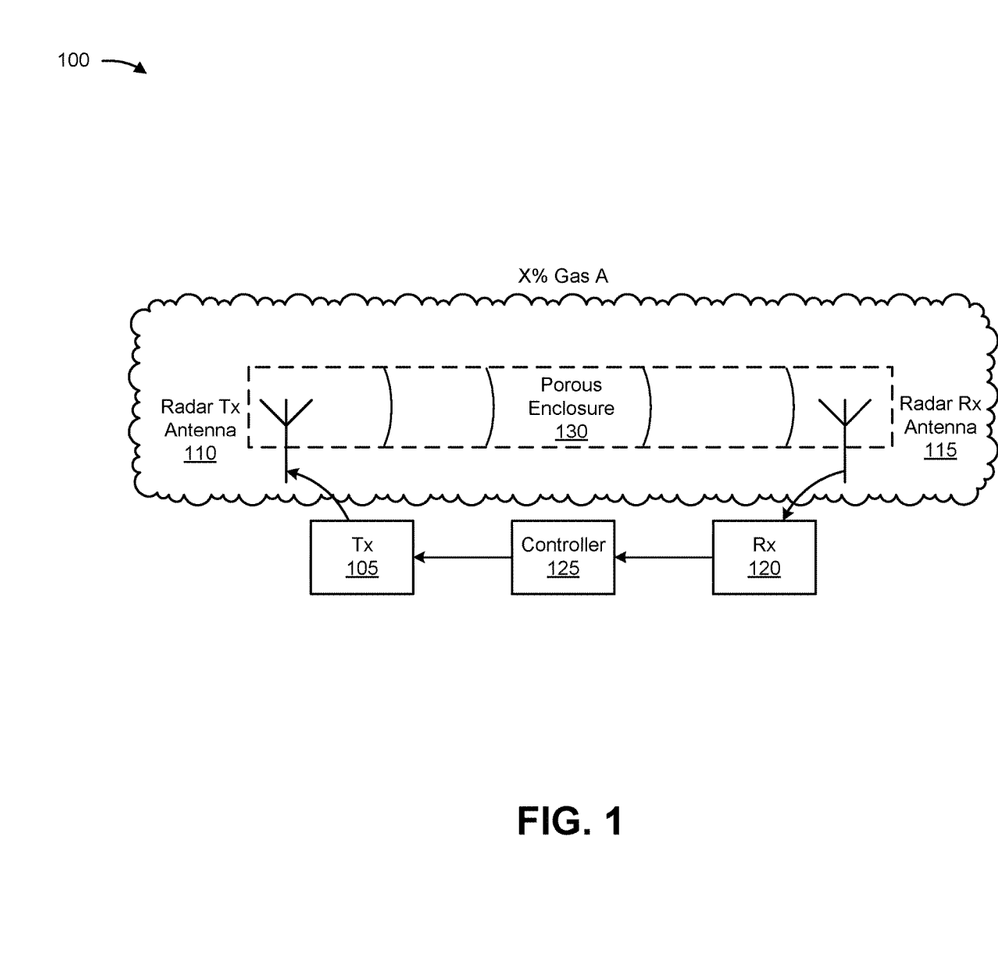
FIG. 1 is a diagram of an example gas sensor capable of measuring a concentration of a gas concentration based on radar spectroscopy.

FIG. 1 is a diagram of an example gas sensor 100 capable of measuring a concentration of a gas based on radar spectroscopy. As shown in FIG. 1, gas sensor 100 may include a transmitter (Tx) 105, a radar transmit antenna (radar Tx antenna) 110, a radar receiver antenna (radar Rx antenna) 115, a receiver (Rx) 120, a controller 125, and (optionally) a porous or partially porous enclosure 130. Also, as shown in FIG. 1, gas sensor 100 may be designed to measure concentration of a particular gas (e.g., gas A).

Tx 105 includes a component capable of generating and transmitting an electrical signal (e.g., controlled by a signal received from controller 125), and transmitting the electrical signal to radar Tx antenna 110. For example, Tx 105 may include a frequency-tunable microelectromechanical system (MEMS) transmitter, a solid state transmitter, or the like, that is capable of generating and/or transmitting an electrical signal to radar Tx antenna 110.

In some implementations, Tx 105 also may include a power amplifier, a low-noise amplifier, a voltage controlled oscillator, and/or other circuitry for providing a time-varying signal to modulate the signal received from controller 125. In some implementations, Tx 105 may be capable of being tuned to a radar frequency based on a signal received from controller 125.

Radar Tx antenna 110 includes a component capable of converting an electrical signal (e.g., received from Tx 105) to a radar signal, and transmitting the radar signal toward radar Rx antenna 115. For example, radar Tx antenna 110 may include a dipole antenna, patch antenna, horn antenna, frequency-tunable antenna or the like, that is capable of converting the electrical signal to a radar signal, and transmitting the radar signal toward radar Rx antenna 115. The antenna may be a formed by metal wires, printed on a PCB, integrated on an IC, MEMS or into its package or the like. Different antenna may be used for different frequency ranges selectable over high frequency switches. As shown in FIG. 1, in some implementations, a transmit portion of radar Tx antenna 110 may be positioned within porous enclosure 130.

Radar Rx antenna 115 includes a component capable of receiving a radar signal (e.g., transmitted by radar Tx antenna 110), converting the radar signal to an electrical signal, and providing the electrical signal to Rx 120 for processing. As shown in FIG. 1, in some implementations, a receive portion of radar Rx antenna 115 may be positioned within porous enclosure 130.

Rx 120 includes a component capable of receiving and/or processing one or more electrical signals (e.g., received from radar Rx antenna 115). For example, radar Rx antenna 110 may include a dipole antenna, patch antenna, horn antenna, frequency-tunable antenna or the like, that is capable of converting the electrical signal to a radar signal, and transmitting the radar signal toward radar Rx antenna 115. The antenna may be a formed by metal wires, printed on a PCB, integrated on an IC, MEMS or into its package or the like. Different antenna my be used for different frequency ranges selectable over high frequency switches. RX 120 is capable of receiving and/or processing an electrical signal, and providing the processed signal to controller 125. In some implementations, Rx 120 may be capable of being tuned to a radar frequency and/or an IR frequency. Rx 120 also may include a power amplifier, a low-noise amplifier, a voltage controlled oscillator, and/or other circuitry for providing a time-varying signal to demodulate the signal received from radar Rx antenna 115. In some implementations, Rx 120 may provide, to controller 125, information associated with a received signal (e.g., such that controller 125 may determine a concentration of one or more gases in porous enclosure 130).

Controller 125 includes a component capable of controlling operation of gas sensor 100. For example, controller 125 may include a microcontroller, a microprocessor, a digital signal processor, an FPGA or the like. In some implementations, controller 125 may be capable of determining a concentration of a gas based on information associated with a transmitted signal (e.g., a radar signal, an IR signal) and information associated with a received signal corresponding to the transmitted signal. In some implementations, controller 125 may include a component that is capable of sending a signal to indicate whether the concentration of the gas has exceeded a threshold.

Porous enclosure 130 includes a component capable of enclosing, containing, guiding, and/or directing a signal (e.g., a radar signal), while permitting a gas to enter a hollow portion of porous enclosure 130. For example, porous enclosure 130 may be a metallic or non-metallic (e.g., a plastic, a dielectric material, or the like) hollow waveguide. In some implementations, porous enclosure 130 forms a waveguide that provides an expansion mode matched to a resonance peak of the gas. Porous enclosure 130 may also incorporate a center wire to form the waveguide in a way similar to a TEM cell.

In some implementations, porous enclosure 130 may include one or more open portions (e.g., holes) capable of allowing one or more gases to enter the hollow portion of porous enclosure 130. In some implementations, a width of the one or more open portions may be less than a wavelength of the radar signal transmitted by radar Tx antenna 110 in order to reduce or eliminate a likelihood that the radar signal will escape the hollow portion of porous enclosure 130.

In some implementations, based on information provided by Tx 105, radar Tx antenna 110 may generate and transmit a radar signal whose frequency corresponds to a resonance peak for the particular gas (e.g., gas A). For example, the radar signal frequency may be 22 or 183 gigahertz (GHz) for $H_2O$, 63 GHz for $O_2$, or the like. In some implementations, molecules of the particular gas may absorb a portion of the energy from the transmitted radar signal (i.e., to create a diminished radar signal), and radar Rx antenna 115 may receive a radar signal corresponding to an amount of energy, associated with the radar signal, that is not absorbed by the particular gas as the signal travels from radar Tx antenna 110 to radar Rx antenna 115. Radar Rx 115 may convert the received radar signal to an electrical or digital signal and provide the electrical or digital signal to Rx 120. Rx 120 may provide information regarding the electrical signal to controller 125. Controller 125 may determine a concentration of the particular gas based on comparing the information regarding the electrical or digital signal and information regarding the transmitted radar signal (i.e., by determining an amount of the radar signal that is absorbed by the gas).

In some implementations, directing the radar signal through porous enclosure 130 may reduce geometric losses and/or increase a signal-to-noise ratio (SNR) (e.g., as compared to a gas sensor without a porous enclosure). Additionally, the width of the one or more open portions being less than the wavelength of the radar signal transmitted by radar Tx antenna 110 may reduce or eliminate the likelihood of the radar signal leaking out of porous enclosure 130.

In some implementations, gas sensor 100 may be capable of measuring concentrations of multiple gases. For example, based on information provided by Tx 105, radar Tx antenna 110 may generate and transmit a first radar signal whose frequency corresponds to a first resonance peak for a first gas (e.g., $H_2O$), and may generate and transmit a second radar signal whose frequency corresponds to a second resonance peak for a second gas (e.g., $O_2$). Molecules of the first and second gases may absorb a first portion of the energy from the first radar signal and a second portion of the energy from the second radar signal, respectively. Here, radar Rx antenna 115 may receive the first radar signal (e.g., corresponding to an amount of energy that is not absorbed by the first gas) and the second signal (e.g., corresponding to an amount of energy that is not absorbed by the second gas), may convert the first and second received signals to first and second electrical or digital signals, and may provide the first and second electrical signals to Rx 120. Rx 120 may provide information regarding the first and second electrical signals to controller 125.

Here, controller 125 may determine a concentration of the first gas and a concentration of the second gas based on the information regarding the first electrical signal (i.e., information associated with the received first radar signal), information associated with the transmitted first radar signal, the information regarding the second electrical signal (i.e., information associated with the received second radar signal), and information associated with the transmitted second radar signal. In some implementations, a same radar Tx antenna 110 and radar Rx antenna 115 may be used to transmit and receive both the first and second radar signals (e.g., when the first frequency, associated with the first radar signal, and the second frequency, associated with the second radar signal, are within a threshold frequency range, such as less than or equal to approximately 20 GHz apart).

The number, arrangement, and/or type of components shown in FIG. 1 are provided as an example. In practice, there may be additional components, fewer components, different components, differently arranged components, and/or different types of components than those shown in FIG. 1. Furthermore, two or more components shown in FIG. 1 may be implemented within a single component, or a single component shown in FIG. 1 may be implemented as multiple, distributed components. Additionally, or alternatively, a set of components (e.g., one or more components) shown in FIG. 1 may perform one or more functions described as being performed by another set of components shown in FIG. 1.

Figure 2:
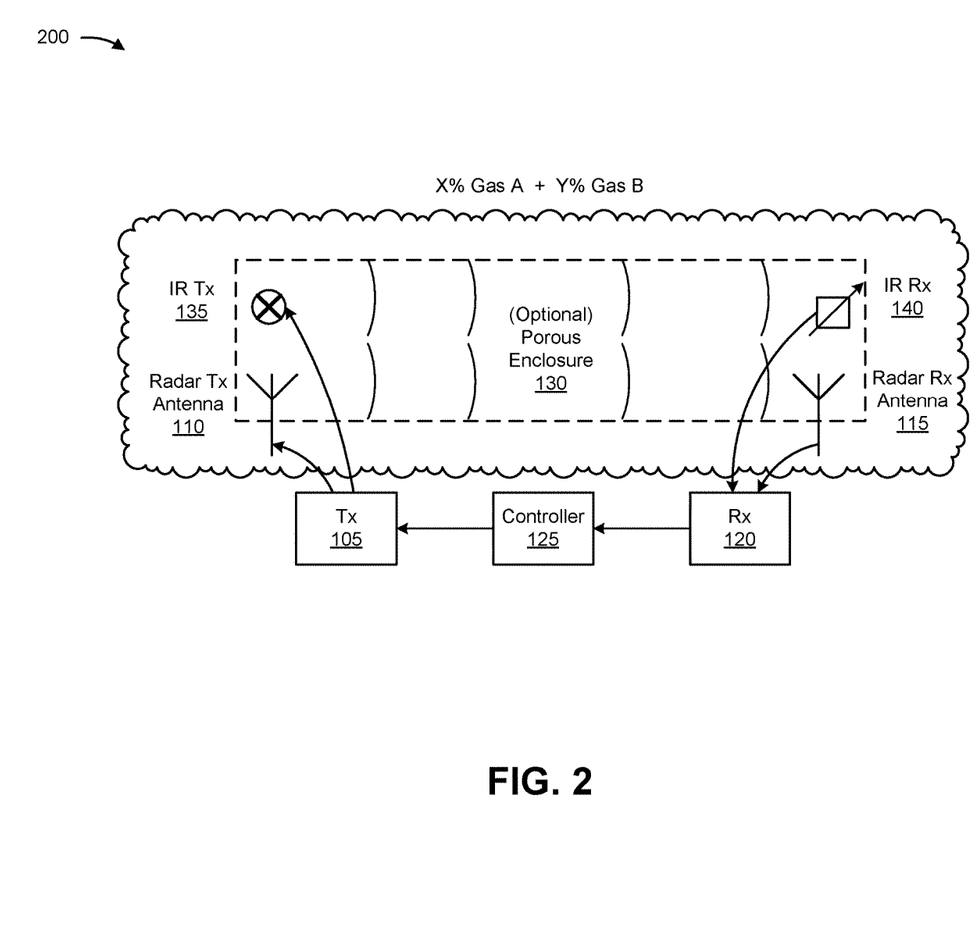
FIG. 2 is a diagram of an example gas sensor capable of measuring a concentration of a gas based on radar spectroscopy and IR spectroscopy.

FIG. 2 is a diagram of an example gas sensor 200 capable of measuring a concentration of a gas based on radar spectroscopy and IR spectroscopy. As shown in FIG. 2, gas sensor 200 may include Tx 105, radar Tx antenna 110, radar Rx antenna 115, Rx 120, controller 125, an IR transmitter (IR Tx) 135, and an IR receiver (IR Rx) 140. As further shown, gas sensor 200 may (optionally) include porous enclosure 130. Also as shown in FIG. 2, gas sensor 200 may be capable of measuring a concentration (e.g., X %) of a first gas (e.g., gas A) and a concentration (e.g., Y %) of a second gas (e.g., gas B).

IR Tx 135 includes a component capable of converting an electrical signal (e.g., received from Tx 105) to an IR signal, and transmitting the IR signal toward IR Rx 140. For example, IR Tx 135 may include an IR emitting diode (e.g. an InAlSb LED), a light bulb, a MEMS radiator or the like. As shown, in some implementations, IR Tx 135 may be positioned within porous enclosure 130.

IR Rx 140 includes a component capable of receiving an IR signal, converting the IR signal to an electrical signal, and providing the electrical signal for processing by Rx 120. For example, IR Rx 140 may include a thermopile, a pyroelectric element, a bolometer resistor, one or more optical fibers, or the like. As shown, in some implementations, IR Rx 140 may be positioned within porous enclosure 130.

In some implementations, based on information provided by Tx 105, radar Tx antenna 110 may generate and transmit a radar signal whose frequency corresponds to a resonance peak for the first gas (e.g., $H_2O$). Additionally, or alternatively, based on information provided by Tx 105, IR Tx 135 may generate and transmit an IR signal whose frequency includes a resonance peak for the second gas (e.g., $CO_2$).

In some implementations, molecules of the first gas may absorb a portion of the energy from the transmitted radar signal, and radar Rx antenna 115 may receive a radar signal corresponding to an amount of energy, associated with the radar signal, that is not absorbed by the first gas as the signal travels from radar Tx antenna 110 to radar Rx antenna 115. Radar Rx antenna 115 may convert the received radar signal to a first electrical signal and provide the first electrical signal to Rx 120. Rx 120 may provide information regarding the first electrical signal to controller 125. Controller 125 may determine a concentration of the first gas based on comparing the information regarding the first electrical signal (i.e., information associated with the received radar signal) and information associated with the transmitted radar signal.

Additionally, or alternatively, molecules of the first gas or the second gas may absorb a portion of the energy from the transmitted IR signal (i.e., to create a diminished IR signal), and IR Rx 140 may receive an IR signal corresponding to an amount of energy, associated with the IR signal, that is not absorbed by the second gas as the signal travels from IR Tx 135 to IR Rx 140. IR Rx 140 may convert the received IR signal to a second electrical signal and provide the second electrical signal to Rx 120. Rx 120 may provide information regarding the second electrical signal to controller 125. Controller 125 may determine a concentration of the second gas based on comparing the information regarding second electrical signal (i.e., information associated with the received IR signal) and information associated with the transmitted IR signal.

Recall from the description above that an IR-based gas sensor may exhibit cross-sensitivity to one or more non-target gases because an IR transmitter may transmit across broadband IR spectrum, thereby reducing an accuracy of a measured concentration for a particular gas. This issue is addressed by gas sensor 200 since controller 125 may subtract the IR absorption effect of the concentration of the first gas (e.g., $H_2O$) from the IR absorption effect of the concentration of the second gas (e.g., $CO_2$), thereby reducing or eliminating the cross-sensitivity of the measurement of the second gas. By eliminating the cross-sensitivity, the concentration of the second gas may be determined more accurately than would be the case if radar-based sensing was not utilized.

The number, arrangement, and/or type of components shown in FIG. 2 are provided as an example. In practice, there may be additional components, fewer components, different components, differently arranged components, and/or different types of components than those shown in FIG. 2. Furthermore, two or more components shown in FIG. 2 may be implemented within a single component, or a single component shown in FIG. 2 may be implemented as multiple, distributed components. Additionally, or alternatively, a set of components (e.g., one or more components) shown in FIG. 2 may perform one or more functions described as being performed by another set of components shown in FIG. 2.

Figure 3:
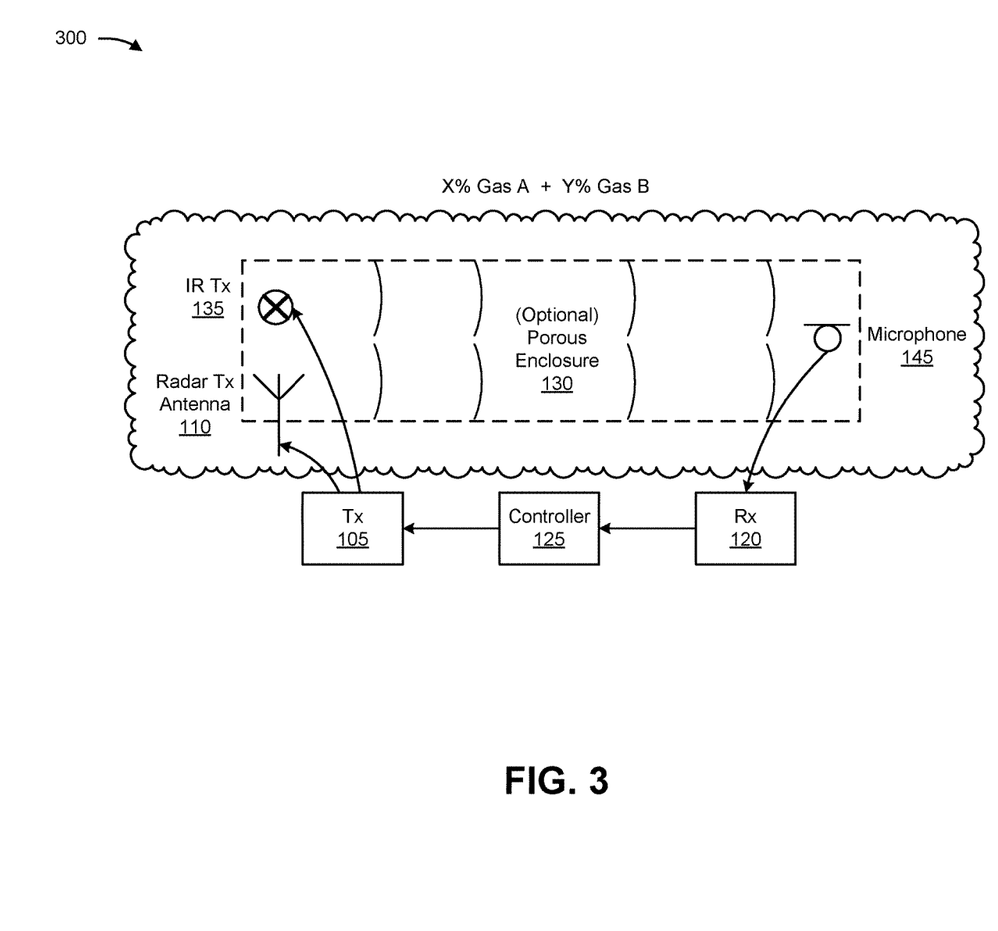
FIG. 3 is a diagram of an additional example gas sensor capable of measuring a concentration of a gas based on radar spectroscopy and IR spectroscopy.

FIG. 3 is a diagram of an additional example gas sensor 300 capable of measuring a concentration of a gas based on radar spectroscopy and IR spectroscopy. As shown in FIG. 3, gas sensor 300 may include Tx 105, radar Tx antenna 110, Rx 120, controller 125, IR Tx 135, and microphone 145. As further shown, gas sensor 300 may (optionally) include porous enclosure 130. Also as shown in FIG. 3, gas sensor 300 may be designed to measure a concentration (e.g., X %) of a first gas (e.g., gas A) and a concentration (e.g., Y %) of a second gas (e.g., gas B).

Microphone 145 includes a component capable of converting sound waves, caused by pressure changes, into an electrical signal. For example, microphone 145 may include a microelectromechanical system (MEMS) microphone that operates using a photoacoustic effect. The photoacoustic effect is the formation of sound waves following light absorption in a material sample (e.g., X % gas A and Y % gas B in porous enclosure 130). Here, absorption of radiation energy (e.g., the IR signal, the radar signal) by a gas causes local heating. This local heating converts into a local change of pressure (in accordance with the general gas equation: pressure x volume/temperature=constant). If the signal is modulated in an acoustic frequency range, the local pressure change can be observed as sound, and thus measured by microphone 145. In some implementations, use of microphone 145 (e.g., a MEMS microphone) provides for high sensitivity and long term stability (e.g., as compared to IR Rx 140). In some implementations, microphone 145 may be encapsulated in a sealed volume of a reference gas.

In order to realize the photoacoustic effect, the intensity of the signal should vary, either periodically (e.g., modulated light) or as a single flash (e.g., pulsed light). The photoacoustic effect is then quantified by measuring the formed sound (e.g., caused by the pressure change within porous enclosure 130) with microphone 145. The time variation of the electric output (e.g., current, voltage) from microphone 145 is a photoacoustic signal and may be used to determine an amount of the signal (e.g., the radar signal, the IR signal) absorbed by the gas within porous enclosure 130.

In some implementations, Tx 105 modulates the radar signal and/or the IR signal in the audio range (e.g., 10 Hz, 15 Hz, 30 Hz, or the like). Tx antenna 110 and/or IR Tx 135 transmit the radar signal and/or the IR signal through the first gas and the second gas in porous enclosure 130. Microphone 145 measures sound (i.e., pressure changes) associated with the first gas and the second gas, and generates the photoacoustic signal based on the time variation of the sound waves detected by microphone 145. Controller 125 may determine a concentration of the first gas and the second gas based on comparing the received photoacoustic signal to the transmitted radar signal and the transmitted IR signal.

In some implementations, the radar signal and the IR signal may be modulated at the same frequency. In such a case, the radar signal and the IR signal may be multiplexed such that the radar signal and IR signal are received by microphone 145 at different times (i.e., such that Rx 120 receives signals, corresponding to the received radar signal and the received IR signal, at different times). In other words, the radar signal and the IR signal may be multiplexed in order to allow for measurement of the radar signal and IR signal to be made sequentially.

Additionally, or alternatively, the radar signal and the IR signal can be modulated at different (e.g., audio) frequencies and transmitted concurrently. In such a case, measurements of the radar signal and the IR signal may be performed concurrently. Here, one or more additional filters may be used by Rx 120 and/or controller 125 to separate the radar signal and IR signal.

As described above, an IR-based gas sensor may experience significant degradation or aging effects. Using microphone 145 (e.g., rather than IR Rx 140) may cause the determination of the concentrations of gases to be more stable and/or suffer less degradation since microphone 145 does not experience significant degradation or aging effects as compared to IR Rx 140.

The number, arrangement, and/or type of components shown in FIG. 3 are provided as an example. In practice, there may be additional components, fewer components, different components, differently arranged components, and/or different types of components than those shown in FIG. 3. Furthermore, two or more components shown in FIG. 3 may be implemented within a single component, or a single component shown in FIG. 3 may be implemented as multiple, distributed components. Additionally, or alternatively, a set of components (e.g., one or more components) shown in FIG. 3 may perform one or more functions described as being performed by another set of components shown in FIG. 3.

Figure 4:
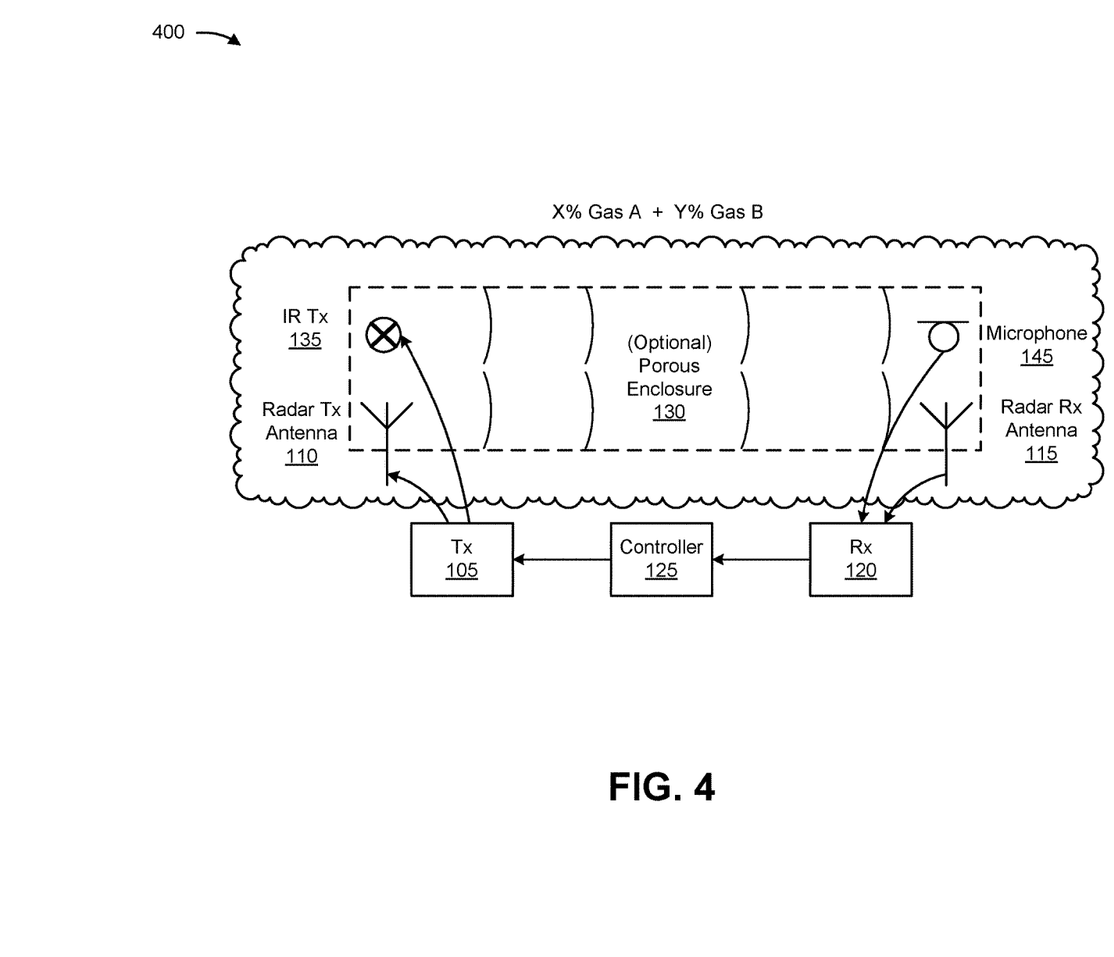
FIG. 4 is a diagram of another example gas sensor capable of measuring a concentration of a gas based on radar spectroscopy and IR spectroscopy.

FIG. 4 is a diagram of another example gas sensor 400 capable of measuring a concentration of a gas based on radar spectroscopy and IR spectroscopy. As shown in FIG. 4, gas sensor 400 may include Tx 105, radar Tx antenna 110, radar Rx antenna 115, Rx 120, controller 125, IR Tx 135, and microphone 145. As further shown, gas sensor 300 may (optionally) include porous enclosure 130. Also as shown in FIG. 4, gas sensor 400 may be designed to measure a concentration (e.g., X %) of a first gas (e.g., gas A) and a concentration (e.g. Y %) of a second gas (e.g., gas B).

In some implementations, based on information provided by Tx 105, radar Tx antenna 110 may generate and transmit a radar signal whose frequency corresponds to a resonance peak for the first gas (e.g., $H_2O$). Additionally, or alternatively, based on information provided by Tx 105, IR Tx 135 may generate and transmit an IR signal whose frequency corresponds to a resonance peak for the second gas (e.g., $CO_2$). Radar Tx antenna 110 and IR Tx 135 transmit the radar signal and the IR signal, respectively, through a first gas and a second gas within porous enclosure 130.

In some implementations, molecules of the first gas may absorb a portion of the energy from the transmitted radar signal (i.e., to create a diminished radar signal), and radar Rx antenna 115 may receive a radar signal corresponding to an amount of energy, associated with the radar signal, that is not absorbed by the first gas as the signal travels from radar Tx antenna 110 to radar Rx antenna 115. Radar Rx 115 may convert the received radar signal to a first electrical signal, and provide the first electrical signal to Rx 120.

Additionally, or alternatively, molecules of the first gas and the second gas may absorb a portion of the energy from the transmitted IR signal (i.e., to create a diminished IR signal), and microphone 145 may measure sound (e.g., pressure changes) associated with the first gas and the second gas, and generate a photoacoustic signal based on the time variation of the sound waves detected by microphone 145. Microphone 145 may convert the photoacoustic signal to a second electrical signal, and provide the second electrical signal to Rx 120.

Rx 120 may receive the first and second electrical signals, and provide information regarding the first and second electrical signals to controller 125. Controller 125 may determine a concentration of the first gas and a concentration of the second gas based on the information regarding the first and second electrical signals (i.e., information associated with the received radar signal, the photoacoustic signal), information associated with the transmitted radar signal, and information associated with the transmitted IR signal.

In some implementations, radar components of gas sensor 400 may be used to calibrate the IR components in gas sensor 400, thereby reducing a drift effect experienced by the IR components over time. For example, an IR-based gas measurement and a radar-based gas measurement may be taken at a particular time (e.g., at start-up of a vehicle), and the radar-based gas measurement may be used to calibrate the IR-based gas measurement (e.g., such that the effect of a first gas, associated with the radar based measurement, is removed from additional (i.e., future) IR-based measurements).

The number, arrangement, and/or type of components shown in FIG. 4 are provided as an example. In practice, there may be additional components, fewer components, different components, differently arranged components, and/or different types of components than those shown in FIG. 4. Furthermore, two or more components shown in FIG. 4 may be implemented within a single component, or a single component shown in FIG. 4 may be implemented as multiple, distributed components. Additionally, or alternatively, a set of components (e.g., one or more components) shown in FIG. 4 may perform one or more functions described as being performed by another set of components shown in FIG. 4.

Implementations described herein provide a radar-based spectroscopic gas sensor that may be used to determine a concentration of a gas. In some implementations, the radar-based spectroscopic gas sensor may be used to determine a concentration of a particular gas. Additionally, or alternatively, the radar-based gas sensor may be used to correct or supplement a determination of a gas concentration measured by an IR-based spectroscopic gas sensor.

The foregoing disclosure provides illustration and description, but is not intended to be exhaustive or to limit the implementations to the precise form disclosed. Modifications and variations are possible in light of the above disclosure or may be acquired from practice of the implementations.

For example, in some implementations, a gas sensor may include multiple IR paths associated with differentiating between multiple different gases. Here, each of the multiple IR paths may including different IR emitters, IR emitters with different filters, and/or may be IR paths which are at least partially lead through an encapsulated reference gas order to permit such differentiation.

As used herein, the term component is intended to be broadly construed as hardware, firmware, and/or a combination of hardware and software.

Some implementations are described herein in connection with thresholds. As used herein, satisfying a threshold may refer to a value being greater than the threshold, more than the threshold, higher than the threshold, greater than or equal to the threshold, less than the threshold, fewer than the threshold, lower than the threshold, less than or equal to the threshold, equal to the threshold, etc.

Even though particular combinations of features are recited in the claims and/or disclosed in the specification, these combinations are not intended to limit the disclosure of possible implementations. In fact, many of these features may be combined in ways not specifically recited in the claims and/or disclosed in the specification. Although each dependent claim listed below may directly depend on only one claim, the disclosure of possible implementations includes each dependent claim in combination with every other claim in the claim set.

No element, act, or instruction used herein should be construed as critical or essential unless explicitly described as such. Also, as used herein, the articles "a" and "an" are intended to include one or more items, and may be used interchangeably with "one or more." Furthermore, as used herein, the term "set" is intended to include one or more items (e.g., related items, unrelated items, a combination of related items, and unrelated items, etc.), and may be used interchangeably with "one or more." Where only one item is intended, the term "one" or similar language is used. Also, as used herein, the terms "has," "have," "having," or the like are intended to be open-ended terms. Further, the phrase "based on" is intended to mean "based, at least in part, on" unless explicitly stated otherwise.

What is claimed is:

1. A gas sensor, comprising:
   a transmitter to:
      transmit a first radar signal, associated with a resonance peak corresponding to a first gas, through a space including the first gas and a second gas,
         the first gas to absorb a portion of the first radar signal to create a second radar signal; and
      transmit a first infrared (IR) signal, associated with a second resonance peak corresponding to the second gas, through the space,
         the first gas or the second gas to absorb a portion of the first IR signal to create a second IR signal; and
   a controller to:
      determine a concentration of the second gas based on the second radar signal and the second IR signal.

2. The gas sensor of claim 1, further comprising:
   multiple IR paths to permit differentiation between multiple gases,
      the multiple IR paths including different IR emitters, IR emitters with different filters, or IR paths which are at least partially lead through an encapsulated reference gas, and
      the second gas being one of the multiple gases.

3. The gas sensor of claim 1, where the first radar signal or the first IR signal is to be transmitted through an enclosure that permits the first gas and the second gas to enter a hollow portion of the enclosure.

4. The gas sensor of claim 3, where the enclosure forms a waveguide that provides an expansion mode matched to the resonance peak of the first gas.

5. The gas sensor of claim 3, where one or more open portions of the enclosure have a width that is less than a wavelength of the first radar signal.

6. The gas sensor of claim 1, further comprising:
   an antenna to receive the second radar signal and an IR receiver to receive the second IR signal.

7. The gas sensor of claim 1, further comprising:
   at least one microphone to measure sound resulting from a pressure change caused by absorption of the portion of the first radar signal by the first gas or absorption of the portion of the first IR signal by the first gas or the second gas.

8. The gas sensor of claim 7, where the at least one microphone is encapsulated in a sealed volume of a reference gas.

9. The gas sensor of claim 1, further comprising:
an antenna to receive the second radar signals; and
a microphone to measure sound resulting from a pressure change caused by absorption of the portion of the first IR signal by the first gas or the second gas.

10. A gas sensor, comprising:
a transmitter to:
convert an electrical signal to a first radar signal associated with a resonance peak corresponding to a gas, and
transmit the first radar signal through a space including the gas,
the gas to absorb a portion of the first radar signal to create a second radar signal,
the first radar signal to be transmitted through an enclosure, during transmission of the first radar signal through the space, that permits the gas to enter a hollow portion of the enclosure; and
a controller to:
determine a concentration of the gas based on the second radar signal.

11. The gas sensor of claim 10, where the resonance peak is a first resonance peak and the gas is a first gas, and where the transmitter is further to:
transmit a first infrared (IR) signal, associated with a second resonance peak corresponding to a second gas, through the space,
the space including the second gas, and
the first gas or the second gas to absorb a portion of the first IR signal to create a second IR signal; and
where the controller is further to:
determine a concentration of the second gas based on the second radar signal and the second IR signal.

12. The gas sensor of claim 11, further comprising:
an antenna to receive the second radar signal and an IR receiver to receive the second IR signal.

13. The gas sensor of claim 11, further comprising:
a microphone to measure sound resulting from a pressure change caused by absorption of the portion of the first radar signal by the first gas or caused by absorption of the portion of the first IR signal by the first gas or the second gas.

14. The gas sensor of claim 11, where the transmitter is to multiplex the transmission of the first radar signal and the first IR signal.

15. The gas sensor of claim 11, where the transmitter is further to:
concurrently transmit the first radar signal and the first IR signal,
the first radar signal and the first IR signal to be modulated at different frequencies.

16. The gas sensor of claim 11, further comprising:
an antenna to receive the second radar signals; and
a microphone to measure sound resulting from a pressure change caused by absorption of the portion of the first IR signal by the first gas or the second gas.

17. A radar-based gas sensor, comprising:
a transmitter to:
transmit a first radar signal, associated with a first resonance peak corresponding to a first gas, through a hollow portion of an enclosure that includes the first gas and a second gas,
the first gas to absorb a portion of the first radar signal to create a second radar signal; and
transmit a first infrared (IR) signal, associated with a second resonance peak corresponding to the second gas, through the hollow portion of the enclosure,
the first gas or the second gas to absorb a portion of the first IR signal to create a second IR signal; and
a controller to:
determine a concentration of the second gas based on the second radar signal and the second IR signal.

18. The radar-based gas sensor of claim 17, further comprising:
an antenna to receive the second radar signal; and
an IR receiver to receive the second IR signal.

19. The radar-based gas sensor of claim 17, further comprising:
a microphone to measure sound resulting from a pressure change caused by absorption of the portion of the first radar signal by the first gas or absorption of the portion of the first IR signal by the first gas or the second gas.

20. The radar-based gas sensor of claim 17, further comprising:
an antenna to receive the second radar signal; and
a microphone to measure sound resulting from a pressure change caused by absorption of the portion of the first IR signal by the first gas or the second gas.

* * * * *